United States Patent [19]

Foslien

[11] Patent Number: 4,477,007

[45] Date of Patent: Oct. 16, 1984

[54] STAPLER WITH INTERMEDIATE LATCHING MECHANISM

[75] Inventor: Floyd L. Foslien, Stillwater, Minn.

[73] Assignee: Minnesota Mining and Manufacturing Company, Saint Paul, Minn.

[21] Appl. No.: 540,112

[22] Filed: Oct. 11, 1983

Related U.S. Application Data

[63] Continuation of Ser. No. 234,999, Feb. 17, 1981, abandoned.

[30] Foreign Application Priority Data

Feb. 22, 1980 [SE] Sweden ............................ 8001387

[51] Int. Cl.³ .......................... B25C 5/02; A61B 17/04
[52] U.S. Cl. ...................................... 227/19; 227/121; 227/DIG. 1
[58] Field of Search ................ 227/19, 121, DIG. 1; 128/334 R, 334 C

[56] References Cited

U.S. PATENT DOCUMENTS

| 2,289,308 | 7/1942 | Fancher et al. | 227/121 |
| 3,873,016 | 3/1975 | Fishbein | 227/121 X |
| 4,043,504 | 8/1977 | Huell et al. | 227/19 X |
| 4,077,557 | 3/1978 | Green | 227/121 X |
| 4,109,844 | 8/1978 | Becht | 227/19 X |
| 4,202,480 | 5/1980 | Annett | 227/121 X |

FOREIGN PATENT DOCUMENTS 711115 10/1941 Fed. Rep. of Germany ...... 227/121

Primary Examiner—Paul A. Bell
Attorney, Agent, or Firm—Donald M. Sell; William L. Huebsch

[57] ABSTRACT

A stapler comprising a ram adapted to engage a staple and move to a formed position so that an end portion of the ram bends the staple closed around the anvil. The stapler comprises latching means for stopping movement of the end portion of the ram away from the anvil at a predetermined position of the ram at which the ram presses the staple against the anvil and end portions of the staple project outwardly of the stapler on opposite sides of the anvil.

2 Claims, 4 Drawing Figures

STAPLER WITH INTERMEDIATE LATCHING MECHANISM

This is a continuation of application Ser. No. 234,999 filed Feb. 17, 1981 now abandoned.

TECHNICAL FIELD

This invention relates to staplers, and in one important aspect to medical staplers of the type in which a ram closes staples around a cantilevered anvil.

BACKGROUND ART

Many staplers are known which comprise a housing having a passageway with an outlet opening; a cantilevered anvil projecting transverse of the passageway at the outlet opening; means for biasing a staple into the passageway; and a ram or driver having an end portion adapted to engage the staple and being mounted within the passageway for sliding movement from a load position with the ram or driver spaced to afford movement of the staple into the passageway, to a formed or ejected position at which the end portion of the driver has bent the staple closed around the anvil at the outlet opening. Such staplers for use in the medical field to staple disunited skin are described, for example, in U.S. Pat. Nos. 3,873,016 and 4,109,844. While such staplers can be effective, the user is required to either position a portion of the stapler adjacent the edges of skin or other material to be stapled and rely on markings on the stapler to indicate where a staple will enter the skin or other material when the stapler is activated, or to partially activate the stapler so that end portions of the staples projecting outwardly of the stapler and to then hold the stapler in this semiactivated state while he positions the end portions of the staple relative to the skin or other material to be stapled. The former approach provides less accuracy of staple placement than is desired for some applications and by some practitioners, whereas the latter is difficult to accomplish with uniformity.

DISCLOSURE OF THE INVENTION

The present invention provides a stapler which can be partially activated to an intermediate position at which it will maintain itself and at which a staple is firmly held at an outlet opening of the stapler with end portions of the staple projecting outwardly of the opening so that the end portions of the staple can be accurately located in the skin or other material to be stapled, and can also be used in the manner of hooks to position such skin or other material in desired positions prior to such stapling.

According to the present invention there is provided a stapler of the aforementioned type which comprises latching means for stopping movement of the end portion of the driver away from the anvil at a predetermined intermediate position of the ram between its load and formed positions only during movement of the driver from its load position toward its formed position at which intermediate position the driver presses the staple against the anvil and end portions of the staple project from the outlet opening on opposite sides of the anvil.

While such means could be incorporated into staplers of the types described in U.S. Pat. Nos. 3,873,016 and 4,043,504, preferably it is incorporated into a stapler of the type taught in U. S. Pat. No. 4,202,480 (the disclosure whereof is incorporated herein by reference) which provides tactile and visual advantages over the aforementioned types of staplers.

Generally in the type of stapler described in U.S. Pat. No. 4,202,480 the driver moves a staple along the passageway from an inlet opening to the outlet opening, and the latch means is incorporated in means for preventing double feeding of staples into the passageway.

BRIEF DESCRIPTION OF DRAWING

The present invention will be more thoroughly explained with reference to the accompanying drawing where like numbers refer to like parts in the several views, and wherein.

DETAILED DESCRIPTION

Figure 1:
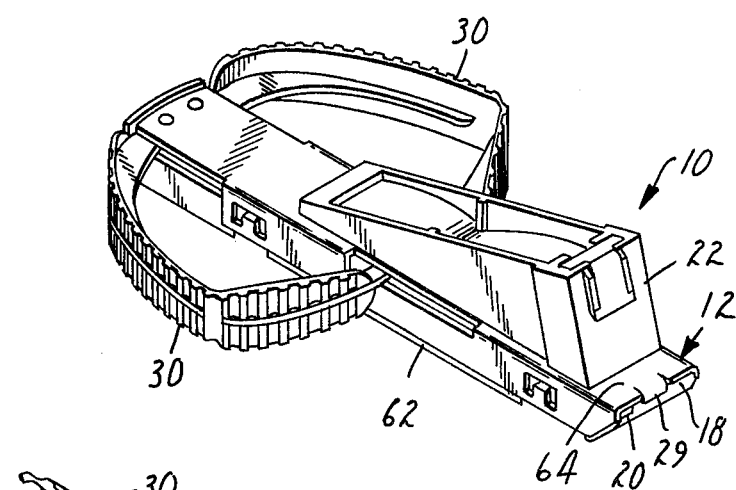
FIG. 1 is a perspective view of a stapler including latching means according to the present invention.

Referring now to the drawing, there is shown a stapler 10 including latching means according to the present invention so that the stapler 10 can be partially activated to an intermediate position at which it holds a staple 24 at an outlet opening 18 of the stapler 10 with generally parallel end portions of the staple 24 projecting outwardly of the stapler 10.

The structure of the stapler 10 is generally the same as the structure of the stapler described in U.S. Pat. No. 4,202,480 (the content whereof is incorporated herein by reference) except for a slightly different shape for a cam 82 of that prior art stapler, and the addition of a recess or notch 11 in the cam 82, which notch 11, in the embodiment illustrated, provides a portion of the latching means according to the present invention; and except that it is preferred to use a staple magazine 22 of the type described in U.S. patent application No. 147,480, and a driver 26 etched on its end as is described in U.S. patent application No. 183,221 (now abandoned), the content of which applications is incorporated herein by reference. The parts of the stapler 10 described in this application has been given the same numbers as parts of the stapler described in U.S. Pat. No. 4,202,480 to facilitate understanding thereof.

Figure 2:
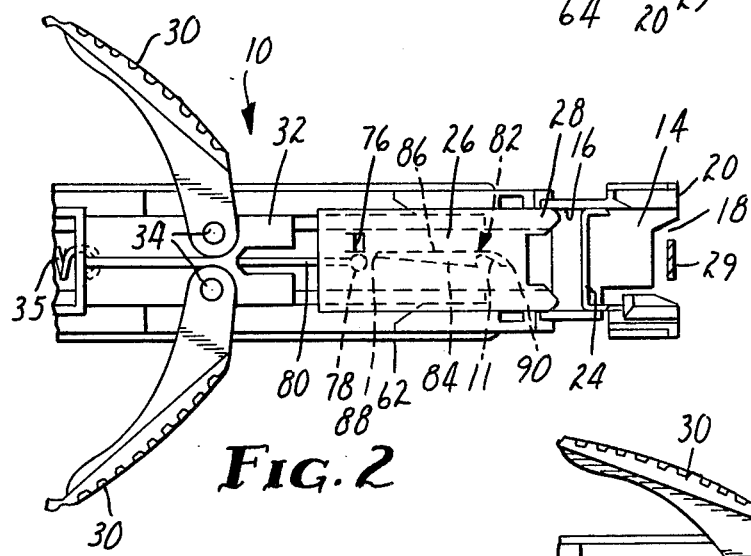
FIG. 2 is an enlarged top view of the stapler shown in FIG. 1 with a driver in the stapler in a load position, and with a staple magazine and a cover of the stapler removed to show detail.

Like the stapler 10 described in U.S. Pat. No. 4,202,480, the stapler 10 shown in the accompanying drawing comprises a housing 12 having a passageway 14 extending from an inlet opening 16 (FIG. 2) to the outlet opening 18 at an end 20 of the housing 12, which passageway 14 is adapted to guide a single staple 24 moved from the inlet opening 16 to the outlet opening 18. The magazine 22 provides means for biasing a stack of the staples 24 into the inlet opening 16, and the driver 26 which has an end portion 28 adapted to engage one of the staples 24 is mounted on the housing 12 for sliding movement (1) from a load position (FIG. 2) with the driver 26 spaced from the inlet opening 16 to afford movement of one of the staples 24 into the passageway 14; (2) along the passageway 14 with the end portion 28 of the driver 26 pushing the staple 24; (3) to the intermediate position (FIG. 3) at which the end portion 28 of the driver 26 has pushed the staple 24 against the cantilevered anvil 29 (which anvil 29 is a portion of a top cover 64 included in the stapler housing 12 and projects across the outlet opening 18), so that the staple 24 is held with parallel end portions of the staple 24 projecting from the stapler 10 on opposite sides of the anvil 29; and (4) then to an eject or formed position (FIG. 4) at which the end portion 28 of the driver 26 has formed the staple around the anvil 29, after which the anvil 29 is retracted from the central portion of the clenched staple 24. The stapler 10 illustrated is particularly adapted for use by surgeons to join disunited skin, which type of skin stapling is well known in the art.

The driver 26 has a length adapted to that portions of the driver 26 will always be positioned adjacent the inlet opening 16 during movement of the driver 26 from its load to its formed position to prevent movement of the adjacent staple 24 in the magazine 22 into the passageway 14 through the inlet opening 16 until the staple 24 already in the passageway 14 is ejected. Drive means manually activatable by pressing opposed flexible handle members 30 together is provided for propelling a drive member 32 (pivotably coupled to adjacent ends of the handle members 30 at pins 34) along the passageway 14 from an initial position (FIG. 2) to an extended position (FIG. 4) to correspondingly move the driver 26 from its load position (FIG. 2) through its intermediate position (FIG. 3) to its formed position (FIG. 4). The handle members 30 are resiliently flexible so that they will tend to return to their original shape when pressure on them is released and a coil spring 35 is coupled between the housing 12 and the drive member 32 so that the drive member 32 is biased to its initial position. The drive member 32 can abut the driver 26 to push the ram 26 from its load position (FIG. 2) through its intermediate position (FIG. 3) to its formed position (FIG. 4), but will not return the driver 26 toward its load position if the drive means is deactivated by removing pressure from the handle members 30 before the driver 26 is pushed entirely to its formed position to prevent a second staple 24 from entering the passageway 14 before the staple 24 already in the passageway 14 is formed and ejected. Means are provided for coupling the drive member 32 to the driver 26 when the handle members 30 have been pressed together sufficiently to move the ram 26 to its formed position, however, so that the driver 26 will subsequently be returned to its load position under the influence of the biasing provided by the spring 35 and the resilience of the handle members 30 when pressure on the handle members 30 is released.

The means for coupling the drive member 32 and the driver 26 when the drive mechanism has positioned the driver in its formed position (FIG. 4) comprises a first lug 76 projecting from one side of the driver 26 and a second lug 78 supported on the drive member 32 for movement transverse of the passageway 14 by a flexible, resilient blade 80 having its end opposite the second lug 78 fixed on the drive member 32. Also included is the elongate cam 82 which is a part of a molded portion 62 of the housing 12, which cam 82 projects centrally into the passageway 14 and provides means (1) for maintaining the second lug 78 in a spaced position out of engagement with the first lug 76 on the driver 26 during movement of the drive member 32 to move the driver 26 from its load toward its formed position; (2) for moving the second lug 78 to an engage position with the lugs 76 and 78 in engagement with each other after the drive member 32 has pushed the driver 26 to its formed position; and (3) for subsequently maintaining the second lug 78 in its engaged position during movement of the drive member 32 and driver 26 back to the load position of the driver 26.

Figure 3:
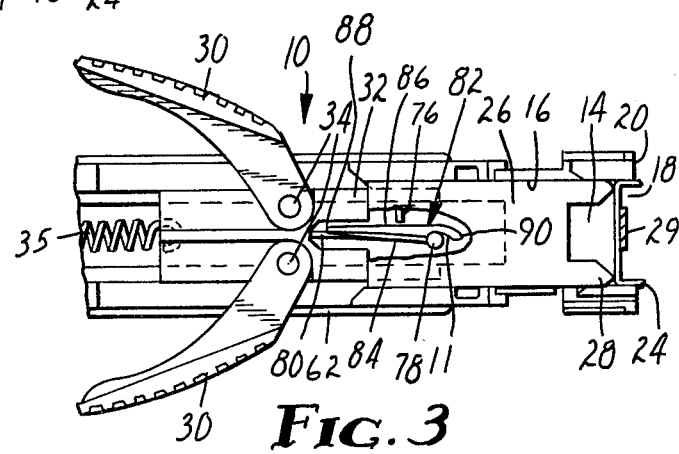
FIGS. 3 and 4 are enlarged fragmentary views similar to that of FIG. 2 but which sequentially show activation of the stapler to engage the latching means according to the present invention (FIG. 3), and to then close a staple (FIG. 4).
Figure 4:
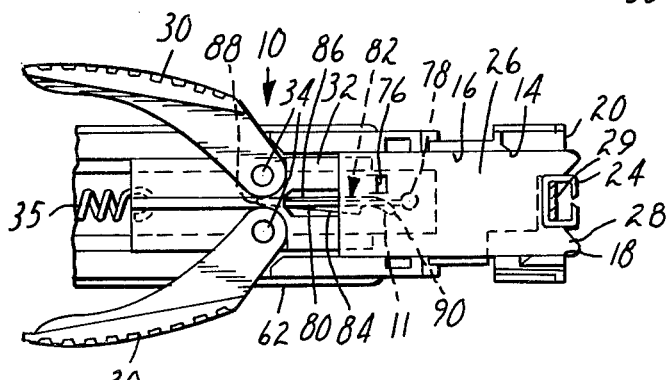

Additionally, the second lug 78, the flexible blade 80 on which the second lug 78 is mounted, the drive member 32 on which the blade 80 is mounted, and the cam 82 with its notch 11 are included in the latching means according to the present invention for stopping movement of the driver 26 away from the anvil 29 at the predetermined intermediate position of the ram 26 between its load and formed positions only during movement of the driver 26 from its load position toward its formed position, at which intermediate position the driver 26 presses the staple 24 against the anvil 29 and parallel end portions of the staple 24 project from the outlet opening 18 of the stapler on opposite sides of the anvil 29 (FIG. 3).

The second lug 78 has an end portion projecting from the end of the blade 80 away from the molded portion 62 of the housing 12, which end portion with the blade 80 can pass along an opening in the housing 12 between the driver 26 and the molded portion 62 of the housing 12 but will engage with the first lug 76. The second lug 78 also has an end portion projecting toward the molded portion 62 of the housing 12 to a position where it will engage surfaces of the cam 82.

Upon manual activation of the stapler 10, the second lug 78 is positioned by the blade 80 so that it will engage an end surface 88 of the cam 82 and will be cammed by the end surface 88 onto a first side surface 84 of the cam 82 out of engagement with the first lug 76 on the driver 26 as the drive member 32 pushes the driver 26 toward its formed position, thereby affording separation of the drive member 32 and the ram 26 if pressure on the handle members 30 is released before the driver 26 is pushed to its intermediate position. Subsequently, when the drive member 32 has pushed the ram 26 to its intermediate position, the second lug 78 will move into the notch 11 under the biasing influence of the blade 80. The notch 11 is generally C-shaped and aligned so that the lug 78 cannot move out of the notch 11 as a result of forces tending to move the lug 78 away from the end 20 of the stapler to thereby latch the drive member 32 and thereby the driver 26 in its intermediate position if forces tending to move the drive member 32 are discontinued at that point. The shape of the notch 11 will, however, cam the second lug 78 out of the notch 11 upon further activation of the drive member 32 to move the driver 26 toward its formed position. Upon such further activation, just before the drive member 32 has completely pushed the ram 26 to its formed position, the second lug 78 moves off the end of the cam 82 and the resilience of the blade 80 positions the second lug 78 adjacent a second end surface 90 of the cam 82. Upon subsequent movement of the drive member 32 back toward its initial position, when manual pressure on the handle members 30 is released, the second lug 78 will engage the cam 82 on its second end surface 90 which will cam the second lug 78 onto a second side surface 86 of the cam 82 and engage the second lug 78 with the first lug 76. The driver 26 will subsequently be pulled back to its load position via engagement of the lugs 78 and 76 as the drive member 32 is returned to its start position under the biasing influence of the spring 35 and the resilient handle members 30.

OPERATION

To operate the stapler 10, a user (such as a surgeon) grasps the stapler 10 around the handle members 30 and squeezes the handle members 30 together to move the drive member 32 away from its initial position (FIG. 2) into engagement with the driver 26, and push the driver 26 from its load position (FIG. 2) toward its eject position (FIG. 3).

As the drive member 32 moves into engagement with the driver 26, the second lug 78 carried on the flexible blade 80 will engage the first end surface 88 of the cam 82 which will cam the second lug 78 onto the first side surface 84 of the cam 82 out of alignment with the first lug 76 on the driver 26. As the user squeezes the handles 30 the drive member 32 drives the driver 26 to engage a single staple 24 and move it along the passageway 14. When the driver 26 has thus moved the staple 24 so that it is pressed against the anvil 29 and the parallel end portions of the staple 24 protrude from the outlet opening 18, the second lug 78 will drop into the notch 11 with an audible click. If the user now release the pressure he is applying to the handle members 30, the drive member 32 and driver 26 will stay in this intermediate position (FIG. 3) at which the user can engage the staple ends with the tissue edges to bring them together for better approximation before finally squeezing the handles 30 to drive the driver 26 to its formed position (FIG. 4) at which the staple 24 is closed and the anvil 29 can be withdrawn from within the closed staple 24.

If the surgeon releases the handles 30 before he has moved the drive member 32 to the position where the second lug 78 engages the notch 11, the resilient handle members 30 will return to their original shape under the biasing influence of the handle members 30 and spring 35, and the second lug 78 will return along the first side surface 84 and first end surface 88 of the cam 82. This allows the drive member 32 and driver 26 to separate and leaves the driver 26 adjacent the staple 24 in the passageway 14 to prevent another staple 24 in the cartridge from entering the passageway 14. Subsequently, if the user again presses the handle members 30 together the drive member 32 will again move into engagement with driver 26 and the second lug 78 will again move along the first end surface 88 and first side surface 84 of the cam 82.

When the user does apply enough force to the handle members 30 to move the driver 26 and lug 78 past the notch 11 fully to the formed position, the second lug 78 will leave the cam 82 so that the resilient blade 80 will position the second lug 78 along the second end surface 90 of the cam 82. A second click is produced when the second lug 78 leaves the cam 82 which gives both a tactile and an audible signal to the user that the staple 24 in the passageway 14 has been fully closed so that the user knows that he can slide the anvil portion 29 from within the closed and ejected staple 24. Subsequent movement of the drive member 32 back to its initial position under the influence of the spring 35 and resilient handle members 30 as the user relaxes his grip on the handle members 30 will cause the second lug 78 to move along the second end surface 90 and second side surface 86 of the cam 82, which moves the second lug 78 into engagement with the first lug 76 on the driver 26. Thus the drive member 32 via the engaged lugs 76 and 78 will pull the driver 26 to its load position as the drive member 32 is returned to its initial position by the spring 35 and handle members 30.

While the present invention has been described with respect to one embodiment thereof, it will be appreciated by those skilled in the art that staplers of other designs may each be modified in accordance with the present invention to provide an intermediate position for their activating mechanism at which a driver in the stapler will position a staple with its end portions projecting from the stapler so that the end portions may be accurately positioned with respect to material into which the staple is to be inserted; and at which, in the case of most medical-type skin staplers, the driver will press the staple against an anvil so that the end portions of the staple may be used in the manner of hooks to locate tissues into which the staple will then be driven. Thus, the scope of the present invention should not be limited by the preferred structure described herein, but only by the structure described by the attached claims and its equivalents.

I claim:

1. In a medical stapler comprising a housing having a passageway extending from an inlet opening to an outlet opening, said openings and passageway being adapted to guide a single staple moved from the inlet to the outlet opening; means for biasing a stack of staples into said inlet opening; an anvil projecting transverse of said passageway at said outlet opening; a driver having an end portion adapted to engage one of the staples and being mounted within said passage for sliding movement between a load position with the driver spaced from the inlet opening to afford movement of one of the staples into the passageway, to a formed position to which the end portion of said driver pushes said staple along said passageway from said inlet opening, at which formed position the end portion of the driver has bent the staple closed around said anvil at said outlet opening, said driver having a length adapted so that a portion thereof will be positioned adjacent said inlet opening during movement of said driver from its load to its formed position to prevent movement of another of said staples into said passageway through said inlet opening; drive means including a driver member and being activatable to move said drive member away from an initial position to move said driver along said passageway, thereby moving one of the staples from said inlet opening through said passageway and to said outlet opening; return means for returning said drive member to its start position after it has moved said driver to its formed position; and coupling means for coupling said drive member and said driver together after said drive member has moved said driver to said formed position so that said driver will be moved back to its load position when said return means returns said drive member to its initial position, said coupling means comprising a first lug fixed to said driver; a second lug; means for supporting said second lug on said drive member for movement between an engage position at which said second lug will engage said first lug to couple said driver with said drive member when said drive member is closely adjacent said driver, and a release position with said lugs separated to afford separation of said driver and said drive member; and cam means for maintaining said lug in said release position during movement of said drive member to move said driver from its load toward its formed position, for moving said lug to its engage position after said drive member has moved said driver to its formed position, and for subsequently maintaining said lug in its engage position as said drive member returns to its initial position to pull said driver from its formed to its load position; the improvement wherein said cam means has a notch for receiving said first lug to provide latching means for stopping movement of the end portion of the driver away from said anvil at a predetermined intermediate position of said driver between its load and formed positions only during movement of said driver from said load position toward said formed position, at which intermediate position the end portion of the driver presses the staple against the anvil and end portions of the staple project from the outlet opening on opposite sides of said anvil so that the end portions of the staple can be accurately located in skin or other material to be stapled, and can also be used in the manner of hooks to position such skin or other material in a desired position prior to bending the staple closed; and to provide means for producing a distinctive audible signal upon engagement of said latching means at said predetermined intermediate position.

2. In a medical stapler according to claim 1 further including the known structure wherein said means for supporting said second lug comprises a resiliently flexible member having said second lug fixed adjacent one end and having a second end fixed on and supported from said drive member, said cam means includes an elongate cam projecting toward said passageway, said cam having opposite first and second surfaces aligned with said passageway and adapted to engage said second lug, with said first surface positioning said second lug in its release position by flexing said resilient member in one direction and said second surface positioning said second lug in its engage position by flexing said resilient member in a direction opposite said one direction, having one end surface shaped and positioned to cam said second lug onto said first surface upon movement of said drive member to move said driver from its load toward its formed position, and having an end surface opposite said one end surface shaped and positioned to cam said second lug onto said second surface upon movement of said drive member toward its load position after said drive member has moved said driver to its formed position, the improvement wherein said notch is formed along said first surface and is shaped for receiving said second lug and preventing movement of said driver away from said anvil, while affording movement of said driver toward said anvil when said drive member moves said driver to said intermediate position where portions of said staple protrude from said outlet opening on opposite sides of said anvil.

* * * * *